United States Patent
Sarrafzadeh et al.

(10) Patent No.: US 10,201,746 B1
(45) Date of Patent: Feb. 12, 2019

(54) NEAR-REALISTIC SPORTS MOTION ANALYSIS AND ACTIVITY MONITORING

(71) Applicant: The Regents of the University of California, Oakland, CA (US)

(72) Inventors: Majid Sarrafzadeh, Anaheim Hills, CA (US); Jack Bobak Mortazavi, Irvine, CA (US); Xiaolong Li, Irvine, CA (US); Kin Chung Chu, San Jose, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1116 days.

(21) Appl. No.: 14/273,413

(22) Filed: May 8, 2014

Related U.S. Application Data (60) Provisional application No. 61/821,171, filed on May 8, 2013.

(51) Int. Cl.
 *A63F 13/00* (2014.01)
(52) U.S. Cl.
 CPC ...... *A63F 13/00* (2013.01); *A63F 2300/1012* (2013.01)
(58) Field of Classification Search
 CPC ....... G06F 3/033; G06F 3/0338; G01C 19/00; G01C 21/206; G01C 21/28; G01P 15/14; G01P 15/18
 See application file for complete search history.

(56) References Cited

U.S. PATENT DOCUMENTS

| | | | |
|---|---|---|---|
| 5,027,303 A | | 6/1991 | Witte |
| 5,430,500 A | * | 7/1995 | Hoshino ............ H04N 7/18 348/666 |

(Continued)

FOREIGN PATENT DOCUMENTS

| | | |
|---|---|---|
| GB | 2351554 A | 1/2003 |
| WO | 0078413 A1 | 12/2000 |

OTHER PUBLICATIONS

Liu et al. 'The Application of an Apparatus of Motion Measurement and Analysis in Freestyle Aerials', 2010, p. 220-224.*

(Continued)

*Primary Examiner* — Elias Desta
(74) *Attorney, Agent, or Firm* — Foley & Lardner LLP; Cliff Z. Liu (57) ABSTRACT

A method and apparatus for the detection, analysis, and identification of realistic human body and limb movements during sports actions for multiple uses comprises collecting the health information of the move, using the moves as a training and monitoring techniques in live usage settings, and as inputs to simulators and video game environments. At least one body-worn sensor transmits values wirelessly to a computing device that records the moves and calculates the health statistics then uses a machine-learning algorithm to analyze and identify the moves. These algorithms then output information and can simulate realistic moves, identify how far from these realistic moves the actual move is, and apply these moves to an electronic game. These algorithms, through various techniques, can distinguish movements, identify many different fine-grain movements, and enforce the full completion of these moves before registering them, thus preventing cheating in a realistic gaming scenario.

35 Claims, 9 Drawing Sheets

(56) References Cited

U.S. PATENT DOCUMENTS

| | | | |
|---|---|---|---|
| 5,459,329 | A | 10/1995 | Sinclair |
| 7,557,731 | B2 | 7/2009 | Ramasubbu |
| 9,436,875 | B2* | 9/2016 | Curcio ............... G06K 9/00718 |
| 2006/0022833 | A1 | 2/2006 | Ferguson et al. |
| 2006/0100781 | A1* | 5/2006 | Lin ..................... G01C 21/28 |
| | | | 701/472 |
| 2008/0098448 | A1* | 4/2008 | Mondesir ......... H04N 21/42201 |
| | | | 725/126 |
| 2008/0190202 | A1* | 8/2008 | Kulach ............. A63B 24/0062 |
| | | | 73/514.01 |
| 2008/0191864 | A1 | 8/2008 | Wolfson |
| 2008/0225041 | A1 | 9/2008 | El Dokor et al. |
| 2008/0318679 | A1 | 12/2008 | Tran et al. |
| 2009/0189874 | A1 | 7/2009 | Chene et al. |
| 2010/0035688 | A1 | 2/2010 | Picunko |
| 2010/0152619 | A1 | 6/2010 | Kalpaxis et al. |
| 2010/0222711 | A1 | 9/2010 | Lajeunesse |
| 2010/0245245 | A1 | 9/2010 | Yamada et al. |
| 2011/0304541 | A1 | 12/2011 | Dalal |
| 2011/0306397 | A1 | 12/2011 | Fleming et al. |
| 2014/0031123 | A1* | 1/2014 | Sarrafzadeh .......... A63F 13/212 |
| | | | 463/36 |

OTHER PUBLICATIONS

Johnson M K et al, Retrographic sensing for the measurement of surface texture and shape, 2009 IEEE Conference on Computer Vision and Pattern Recognition, Miami Beach Florida USA, Jun. 20, 2009, pp. 1070-1077, XP03607061, ISBN: 978-1-4244-3992-8.

Nagata K et al, Feature detection with an image based compliant tactile sensor, Proceedings of the 1999 I EEE/RSJ International Conference on Intelligent Robots and Systems. (IROS'99). Human and Environmental Friendly Robots With Intelligence and Emotional Quotients, Kyongju, Korea Oct. 17, 1999, pp. 838-843, XP002175226, ISBN 978-0-783-5185-1.

* cited by examiner

NEAR-REALISTIC SPORTS MOTION ANALYSIS AND ACTIVITY MONITORING

CROSS-REFERENCE TO RELATED APPLICATIONS

This application claims priority to U.S. Provisional Application Ser. No. 61/821,171, filed May 8, 2013, entitled "NEAR-REALISTIC SPORTS MOTION ANALYSIS AND ACTIVITY MONITORING," which is hereby incorporated by reference as if set forth herein.

FIELD OF THE INVENTION

The present invention relates to the detection, analysis and identification of realistic human body and limb movements. More particularly, the present invention relates to systems, apparatuses and methods of detecting and reproducing motions as inputs to simulators and live video game environments.

BACKGROUND OF THE INVENTION

Motion tracking systems exist in various shapes and forms and all have a form of targeted end application. These systems range from video game systems like the Nintendo® Wii® and the Microsoft® Kinect®, that attempt to take human movement and use it as an input to a video game, to systems that track motion and give feedback on certain sports swings. Most motion tracking systems target one application and limit the range of motions they attempt to track. Particularly, there is a need for a system that detects and classifies body movements, particularly movements of the limbs in action settings.

SUMMARY OF THE INVENTION

Embodiments of the invention utilize body worn sensors to track human motion in realistic and near realistic sports settings and utilizing an algorithm apply this information to a range of applications. The algorithm and system of body-worn sensors use the human body as a computing device input in order to analyze human movement, give training information based upon human movement, and apply this movement to various end applications.

In one aspect, a system for detecting and analyzing motion comprises an attachment member for coupling to a portion of a user's body, an acceleration module coupled to the attachment member and programmed to detect accelerations of the attachment member along three orthogonal directions and to translate the accelerations into corresponding acceleration values, a velocity converter programmed to convert the acceleration values into velocity values along the three orthogonal directions, and a movement detector programmed to translate the velocity values into three-dimensional movement. In some embodiments, the movement detector differentiates between a realistic three-dimensional movement and an attempted cheating of the movement. In some embodiments, the system comprises a pressure sensor coupled to the attachment member for providing pressure values to the velocity converter. In some embodiments, a reset module resets the velocity values when a reset condition is satisfied. In some embodiments, the reset condition comprises the pressure sensor contacting a surface. Alternatively, the reset condition comprises all the acceleration values being within a pre-determined range. In some embodiments, the system comprises a gyroscope, wherein the reset module is programmed to adjust for gravity accelerations and the gyroscopic values to estimate the three dimensional position of the acceleration module. A transmitter of the system wirelessly transmits the acceleration values to the velocity converter. In some embodiments, a classification module is programmed to classify the three-dimensional movement into classified movement. In some of these embodiments, the classification module is programmed to classify the three-dimensional movement using a machine learning algorithm or inference processing. For example, in some embodiments, the classification module is programmed to classify the three-dimensional movement based on a pattern of the velocity values, a direction of the velocity values, or a magnitude of the velocity values. The classified movement can comprise a sports movement. For example, the classified movement can comprise a soccer movement, a football movement, a basketball movement, a running movement, a tennis movement, or a baseball movement. In some embodiments, a health monitoring module is programmed to determine health-related statistics from the three-dimensional movement. In some embodiments, an interface is programmed to map the three-dimensional movement to movement for an application. In some embodiments, the application comprises a video game application, a health-monitor application, an animation application, a simulation application, or a scoring application for scoring the three-dimensional movement against a defined template.

In another aspect, a method of detecting and analyzing motion comprises detecting an acceleration of a body-worn sensor in one of three orthogonal directions, translating the acceleration into a corresponding acceleration value, calculating a velocity value based upon the acceleration of the body-worn sensor, and determining a three-dimensional physical movement based upon the calculated velocity value. In some embodiments, the method further comprises differentiating between a realistic three-dimensional movement and an attempted cheating of the movement. In some embodiments, the method comprises a receiving a pressure value from a pressure sensor. In some embodiments, the velocity is reset when a reset condition is satisfied. The reset condition can comprise the pressure sensor contacting a surface. Alternatively, the reset condition comprises all the acceleration values being within a pre-determined range. In some of these embodiments, the reset condition comprises adjusting for gravity accelerations and gyroscope values to estimate a three-dimensional position of a sensor. In further embodiments, the method comprises classifying the three-dimensional movement into classified movement. Particularly, the movement can be classified into three-dimensional movement using a machine learning algorithm or inference processing. In some embodiments, the movement is classified into three-dimensional movement based on a pattern of the velocity values, a direction of the velocity values, or a magnitude of the velocity values. In some embodiments, the method comprises a sports movement. For example, In some embodiments, the classified movement comprises a soccer movement, a football movement, a basketball movement, a running movement, a tennis movement, or a baseball movement.

In a further aspect, a method of detecting and analyzing realistic motion for different end application goals comprises reading wireless data, filtering the data, with some preliminary cheating prevention checks, processing the data, applying a classification to the data, based upon the classification, determining whether the data indicates a valid three-dimensional physical movement, including whether the movement is a valid movement or an attempted cheating movement generated from non-realistic motion, and based on a determination that the movement is valid, outputting a characteristic of the movement. In some embodiments, reading the data comprises detecting an acceleration of a body-worn sensor in one of three orthogonal directions and reading the acceleration data from the body-worn sensor. In some embodiments the classification comprises a machine learning algorithm or an inference processing classification.

DETAILED DESCRIPTION

The following description is presented to enable one of ordinary skill in the art to make and use the invention and is provided in the context of a patent application and its requirements. Various modifications to the described embodiments will be readily apparent to those skilled in the art and the generic principles herein can be applied to other embodiments. Thus, the present invention is not intended to be limited to the embodiment shown, but is to be accorded the widest scope consistent with the principles and features described herein.

In some embodiments, the steps of the present invention are embodied in machine-executable instructions. These instructions can be used to cause a general-purpose or special-purpose processor that is programmed with the instructions to perform the steps of the present invention. Alternatively, the steps of the present invention might be performed by specific hardware components that contain hardwired logic for performing the steps, or by any combination of programmed computer components and custom hardware components.

The present invention can be provided as a computer program product that can include a machine-readable medium having stored thereon instructions that can be used to program a computer (or other electronic devices) to perform a process according to the present invention. The machine-readable medium can include, but is not limited to, ROMs, RAMs, magnet or optical cards, or other type of media/machine-readable medium suitable for storing electronic instructions.

Various aspects of the disclosure are described through the use of flowcharts. Often, a single instance of an aspect of the present disclosure is shown. As is appreciated by those of ordinary skill in the art, however, the protocols, processes, and procedures described herein can be repeated continuously or as often as necessary to satisfy the needs described herein. Additionally, it is contemplated that process steps can be performed in a different order than the order illustrated in the flowcharts unless otherwise disclosed, either explicitly or implicitly.

Furthermore, it is contemplated that any features from any embodiment can be combined with any features from any other embodiment. In this fashion, hybrid configurations of the disclosed embodiments are well within the scope of the present invention.

Embodiments of the invention are directed to a method and apparatus for the detection, analysis, and identification of realistic human body and limb movements during sports actions for multiple uses comprises collecting the health information of the move, using the moves as a training and monitoring techniques in live usage settings, and as inputs to simulators and video game environments. At least one body-worn sensor transmits values wirelessly to a computing device that records the moves and calculates the health statistics then uses a machine-learning algorithm to analyze and identify the moves. These algorithms then output information and can simulate realistic moves, identify how far from these realistic moves the actual move is, and apply these moves to an electronic game. These algorithms, through various techniques, can distinguish movements, identify many different fine-grain movements, and enforce the full completion of these moves before registering them, thus preventing cheating in a realistic gaming scenario.

Figure 1:
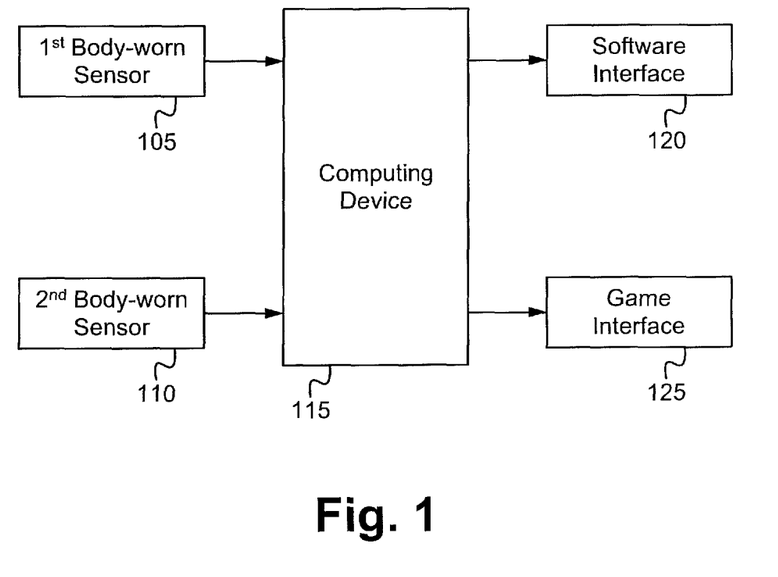
FIG. 1 illustrates a schematic view showing the components of a system for detecting and analyzing motion in accordance with some embodiments.

Referring now to FIG. 1, a system for detecting and classifying body movements is depicted therein. The system 100 is configured for detecting and classifying the movements of limbs in an action setting. As shown in FIG. 1, the system 100 comprises a first body-worn sensor 105, a second body-worn-sensor 110 and a computing device 115. The first body-worn sensor 105 and the second body-worn sensor 110 are configured to couple to a portion of a user's body. Once coupled to the body, the first body-worn sensor 105 and the second body-worn sensor 110 detect an acceleration of the sensor about an axis. For example, in some embodiments, the first body-worn sensor 105 and the second body-worn sensor 110 detect an acceleration along the x-axis, the y-axis, and the z-axis. In some embodiments, the first body-worn sensor 105 and the second body-worn sensor 110 comprise a hand-mounted sensor and a foot-mounted sensor. As shown in FIG. 1, the system 100 comprises two body-mounted sensors, however, the system is able to comprise any appropriate number of sensors depending upon the desired application. By placing motion sensors on the body, initial parameters are gained from the movement of the sensors and decisions are able to be made based upon those movements. The sensors can be placed on various parts of different limbs and can work independently or as a set of devices.

After detecting an acceleration, one or both of the first body-worn sensor 105 and the second body-worn sensor 110 send a wireless signal to the computing device 115. The computing device 115 processes the signal from the first body-worn sensor 105 and the second body-worn sensor 110 and sends a signal to a software interface 120 and/or a game interface 125. Once the data is transmitted from the one or body-worn sensors to the computing device 115, the computing device 115 performs data processing algorithms in order to interpret the movement. Initially the signals from the one or more sensors are filtered to reduce noise and machine learning algorithms are run in order to properly classify the movements. The classification algorithms determine a wide range of realistic human limb motion and particular statistics about those motions, including the strength of the motion, its duration, and a comparison to what is considered an ideal motion.

Figure 2A:
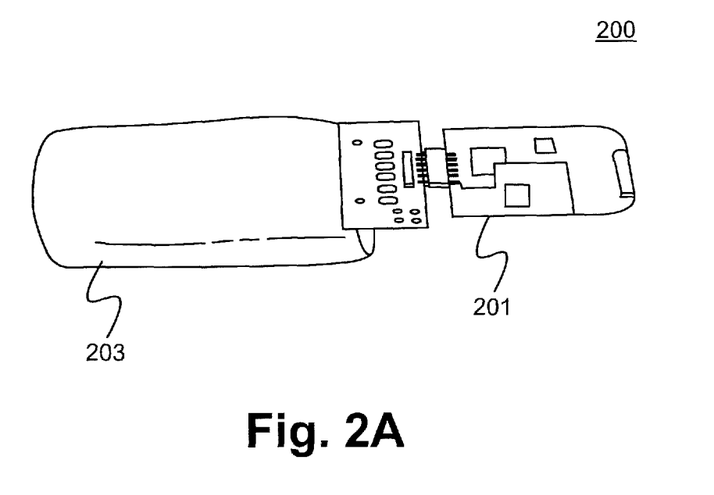
FIG. 2A illustrates a body-worn sensor in accordance with some embodiments.

FIG. 2A illustrates a body-worn sensor which is able to detect an acceleration of a body part. As shown within FIG. 2A, the body-worn sensor 200 comprises an attachment member 203 for attaching to a portion of a user's body and an acceleration module 201 programmed to detect an acceleration of the attachment member 203 and to translate the acceleration into a corresponding acceleration value. In some embodiments, the acceleration module 201 is able to sense an acceleration of the attachment member 203 along three orthogonal directions such as along the x-axis, the y-axis, and the z-axis. In some embodiments, the body-worn sensor comprises a three-axis accelerometer. As described above, the body-worn sensor 200 detects an acceleration of the attachment member 203 and transmits a wireless signal a computing device based upon the detected acceleration.

Figure 2B:
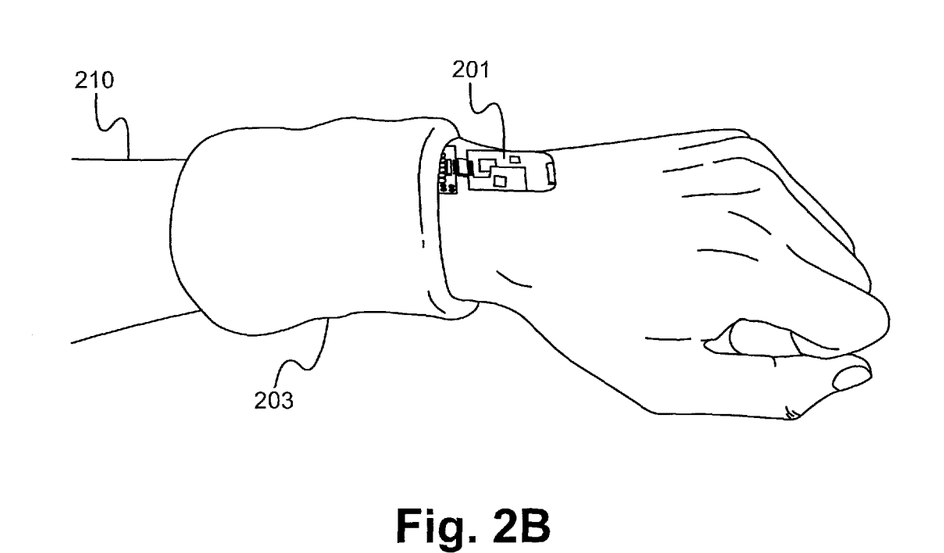
FIG. 2B illustrates a body-worn sensor being worn on a wrist of a user in accordance with some embodiments.

FIG. 2B illustrates the body-worn sensor 200 worn by a user. As shown by FIG. 2B, the attachment member 203 has been placed on an arm 210 of the user. Although the attachment member 203 is shown as a band, which has been placed over the arm 210 of the user, the attachment member 203 is able to comprise any appropriate mechanism configured to couple the acceleration module 201 to the body of the user. When the attachment member 203 is placed on the arm 210, the acceleration module 201 is able to detect an acceleration of the arm 210. For example, the acceleration module 201 is able to detect an acceleration of the arm along the x-axis, the y-axis, and the z-axis as the user moves the arm 210. Based upon the movement of the arm and the corresponding acceleration of the attachment member 203, a wireless signal is sent to a computing device, such as described above.

Figure 3:
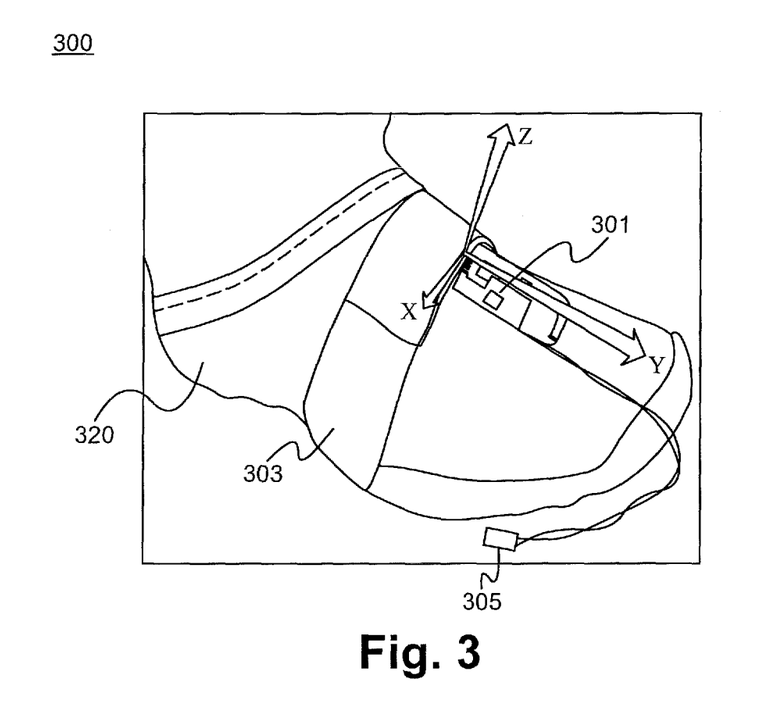
FIG. 3 illustrates a body-worn sensor in accordance with some embodiments.

As shown within FIG. 3, a body-worn sensor is coupled to a shoe 320. The body-worn sensor 300 comprises an attachment member 303, an acceleration module 301, and a pressure sensor 301. In some embodiments, the attachment member 303 loops over and attaches to the foot 320 by a hook and loop attachment. However, the attachment member 303 is able to comprise any appropriate mechanism configured to couple the acceleration module 301 to the body of the user. When the attachment member 303 is placed on the foot 320, the acceleration module 301 is able to detect an acceleration of the foot 320. For example, the acceleration module 301 is able to detect an acceleration of the along the x-axis, the y-axis, and the z-axis as the foot 320 is moved. Based upon the movement of the foot 320 and the acceleration module 301, a wireless signal is sent to a computing device 115, such as (FIG. 1) described above. As further shown within FIG. 3, the body-worn sensor 300 comprises a pressure sensor 305. The pressure sensor 305 identifies when the foot is at rest.

The body-worn sensor 300 is attached to the foot by an attachment member 303 such as a strap, with the pressure sensor 305 under the foot and the acceleration module 301 is coupled at the top of the foot 320. In some embodiments, the body-worn sensor 300 comprises a three-axis accelerometer. The body-worn sensor 300 uses a combination of a force-resistive pressure sensor 305 and an accelerometer 301 that is strapped to a user's foot and can wirelessly transmit foot and leg movements to the computing device. In standard systems, accelerometers are too noisy to reliably determine the velocity information, so the system uses the pressure sensor 305 as a ground truth to identify when the foot 320 is at rest to force the calculated velocities back to zero in order to increase the reliability of the readings.

As described above, the body-worn sensors can be placed on various parts of different limbs and can work independently or as a set of devices and communicate wirelessly to a computing device that will run various data processing algorithms and then can provide different end applications for this data. The sensing devices can range from simple body-worn accelerometers to a fusion of devices ranging from pressure to angular velocity detection or magnetic field orientation.

Using the one or more body-worn sensors, body movement is obtained and received wirelessly at a computing device. For example, in some embodiments, human body and limb movements are obtained wirelessly via a Bluetooth® radio or a Zigbee®-compliant radio (SimpliciTI®) from Texas Instruments®. In some embodiments, the data received at the computing device is low-pass filtered through the use of a sliding window averaging technique. Once filtered, velocity information is obtained from the accelerations in order to determine the strength and range of motion. Velocity information can then used as an input to a classification system where health statistics are gathered and input is given to a computer video game such as Electronic Arts' FIFA® Soccer Series and 2K Sports' NBA Series.

The data processing algorithms themselves can allow for a wide range of functions. The signals can be filtered and passed directly to classifiers to identify movement, or a series of algorithms can be run in order to determine what kind of sports actions are being undertaken, and the relative strengths, accuracies, and health information of the sports actions. Particularly, the system must identify the move, also the strength of such move to see if it is a viable sports move, or an attempted cheating of the realistic-motion requirement, and, if applying this to a training environment or a sports game, the system must ensure that the user has not tried to cheat the move but actually participated in it.

Additionally, by placing accelerometers and other sensors on the leg and an accelerometer on the hand, the system can identify limb movements in three different directions: x, y, and z when playing, for example, a soccer game or a basketball game.

Figure 4:
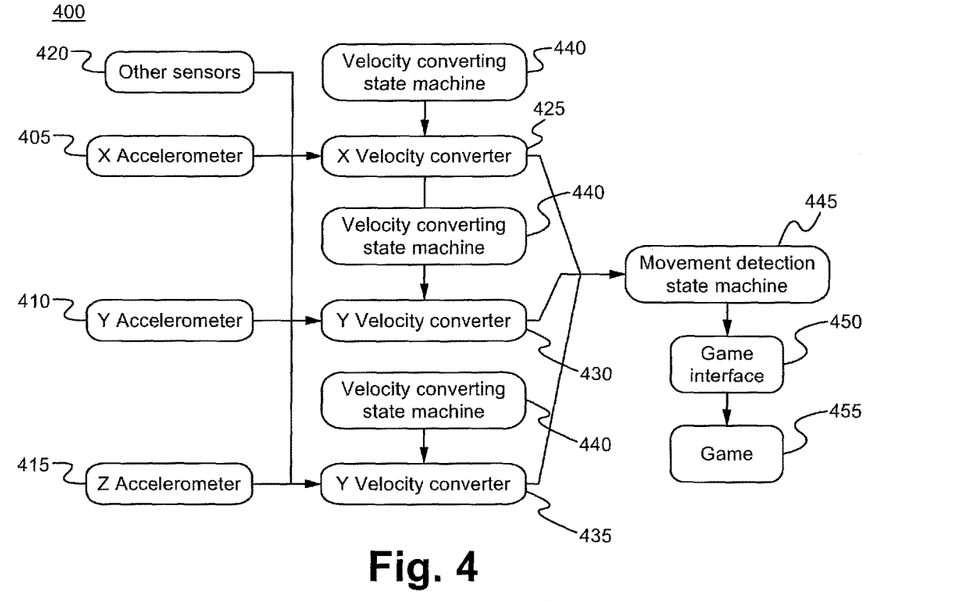
FIG. 4 illustrates a schematic view showing the components of a system for detecting and analyzing motion in accordance with some embodiments.

FIG. 4 illustrates a illustrates a schematic view of the components of the system for detecting and analyzing motion as it detects and classifies body movements. As described above, in some embodiments, the one or more body-worn sensors comprise a three-axis accelerometer for detecting an acceleration of a body part and sending a wireless signal to a computing device. The accelerometer detects a x-accelerometer value 405, a y-accelerometer value 410 and a z-accelerometer value 415. Based upon each accelerometer value, a corresponding signal is sent to a x-velocity converter 424, a y-velocity converter 430 and a z-velocity converter 435. Each velocity converter also receives a signal from a velocity converting state machine 440. In some embodiments, each velocity converter also receives input from one or more additional sensors, such as a pressure sensor. Based upon the accelerometer value and the input received from the velocity converting state machine 440, a velocity value is determined along the x-axis, the y-axis, and the z-axis and a signal is sent to a movement detection state machine 445. The movement detection state machine 445 translates the velocity values into a three-dimensional movement and passes the movement to the game interface 450 and the final result is shown on the game 455.

Figure 5:
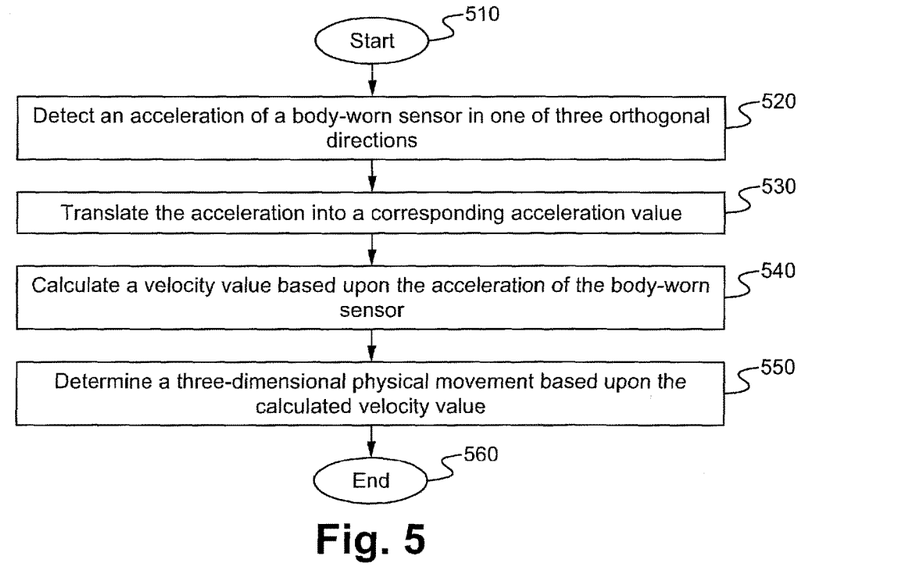
FIG. 5 illustrates a flow chart for detecting and analyzing motion in accordance with some embodiments.

FIG. 5 illustrates a method of detecting and analyzing motion in accordance with the components of the system, such as described above. The method begins in the step 510. In the step 520, an acceleration of a body-worn sensor is detected in one of three orthogonal directions. Then, in the step 540, a velocity value is calculated based upon the acceleration of the body-worn sensor. Based upon the calculated velocity value, a three-dimensional physical movement is determined in the step 550. The method ends in the step 560. In some embodiments, the method further comprises receiving a pressure value from a pressure sensor. In some embodiments, the velocity value is reset when a reset condition is satisfied. For example, in some embodiments, the reset condition comprises the pressure sensor contacting a surface. Alternatively, the reset condition comprises all of the acceleration values being within a predetermined range. The reset module is programmed to adjust for gravity acceleration along the three orthogonal directions.

In some embodiments, the three-dimensional movement is classified. For example, in some embodiments, the movement is classified using a machine learning algorithm or inference processing such as described above, and below. In some embodiments, the movement is classified into three-dimensional movement based on a pattern of the velocity values, a direction of the velocity values, or a magnitude of the velocity values. In some embodiments, the classified movement comprises a soccer movement, a football movement, a basketball movement, a running movement, a tennis movement, or a baseball movement.

As described above, in some embodiments, the one or more body-worn sensors comprise a 3-axis accelerometer which wirelessly communicates via a Bluetooth® radio or a Zigbee®-compliant radio (SimpliciTI®) from Texas Instruments®. In some embodiments, the one or more body-worn sensors employ a polling method to use the Zigbee protocol when transmitting the data. After the signal is read from the one or more body-worn sensors, a series of filters are preferably used to filter the signal read from the accelerometer and/or the pressure sensor. This ensures that noise is reduced and provides a more accurate reading representing the physical movement. Additionally, filtering the data converts the raw values into a range, which is usable for the rest of the system.

In some embodiments, each axis of the accelerometer is filtered separately using a sliding window technique of average values to reduce effects of noise. When the body-worn sensor is placed on a foot, each axis value is normalized to zero at rest with one axis having a normalized value to represent acceleration due to fighting gravity. Since the sensor is placed on the surface of the foot, and the surface of the foot is not flat, the sensor reading is preferably adjusted. When the one or more body-worn sensors are placed on either of the foot or the hand, a filter is used to calculate tilt angles of the device and calibrate the sensor as if it is placed on a flat horizontal surface.

As described above, a velocity value is calculated for the x-axis, the y-axis, and the z-axis. The acceleration for each of the axises is integrated in order to obtain the velocity for each axis. However, due to vibration, which can be caused by sudden stop and start of the body movement, the accelerometer might get a non-zero reading even if the body part is not actually accelerating. As a result, when acceleration is integrated in order to obtain the velocity, the velocity value can easily get to infinity or a non-realistic large value. In order to correct this problem, the velocity must be adjusted back to a reasonable range. As stated above, in some embodiments, pressure sensor readings can be used in order to force the velocity value back to zero such as if the player's foot is on the ground. With the player's foot on the ground it can be presumed the velocity is zero because humans usual do not drag their feet while moving in sports settings and environments.

In some embodiments, when the body-worn sensor is worn on a hand, a gyroscope can be used in order to actively calibrate the tilted sensor to adjust for gravity acceleration. In some embodiments, a button coupled to the body-worn sensor may be pressed to issue a speed adjustment. Particularly, this extra freedom given to the user will likely not sacrifice cheating prevention since the user cannot cheat the system or get any benefit by resetting the velocity back to zero. In yet another embodiment, no extra input is needed. The acceleration itself tells the system whether the device stops moving and triggers a velocity adjustment. This can be done by recognizing a segment of the acceleration waveform where the values all fall into a pre-set threshold, with the assumption that the body should not move slowly and constantly.

Figure 7A:
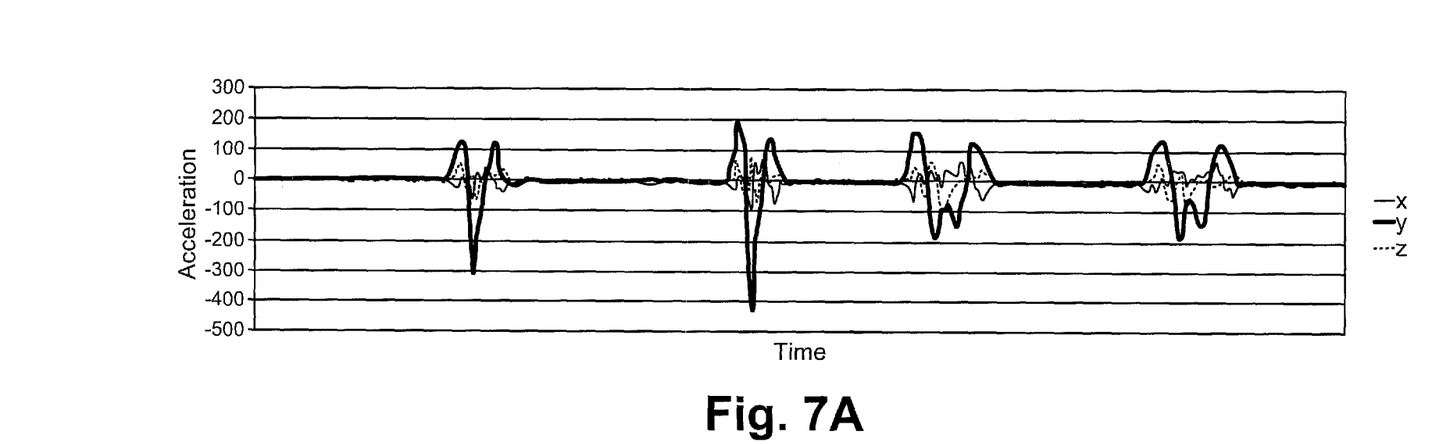
FIG. 7A illustrates a graph showing a signal depicting acceleration over time of a body-worn sensor worn on an arm in accordance with some embodiments.

As shown in FIG. 7A, an acceleration signal is depicted for a body-worn sensor worn on the arm. The Y values refer to forward movement. The acceleration values are raw values detected by the accelerometer based upon four forward movements of the arm. The first two movements are small but fast movements, while the third and fourth are complete forward movement of the arm, extended fully outward and back. The second movement shows that maximum value among all four movements.

After calculating the velocity values for the x-axis, the y-axis, and the z-axis, those values are used in order to determine which direction a user is moving. This data is utilized in order to realize an initial move conclusion. This can determine a more general result of a movement which is not restricted to one axis. This can also distinguish between a movement in one direction and a different diagonal movement. The velocity value can then be used to determine the strength or duration of the physical movement. Unlike acceleration, time is essential when calculating velocity. The duration of the acceleration will directly influence the velocity value. As a result, it is possible to distinguish between small movements and large movements and guarantee the user is completing the move instead of creating an acceleration spike. This can be done because a large movement generates a large velocity value even though both small and large movements can produce a large acceleration signal.

Figure 7B:
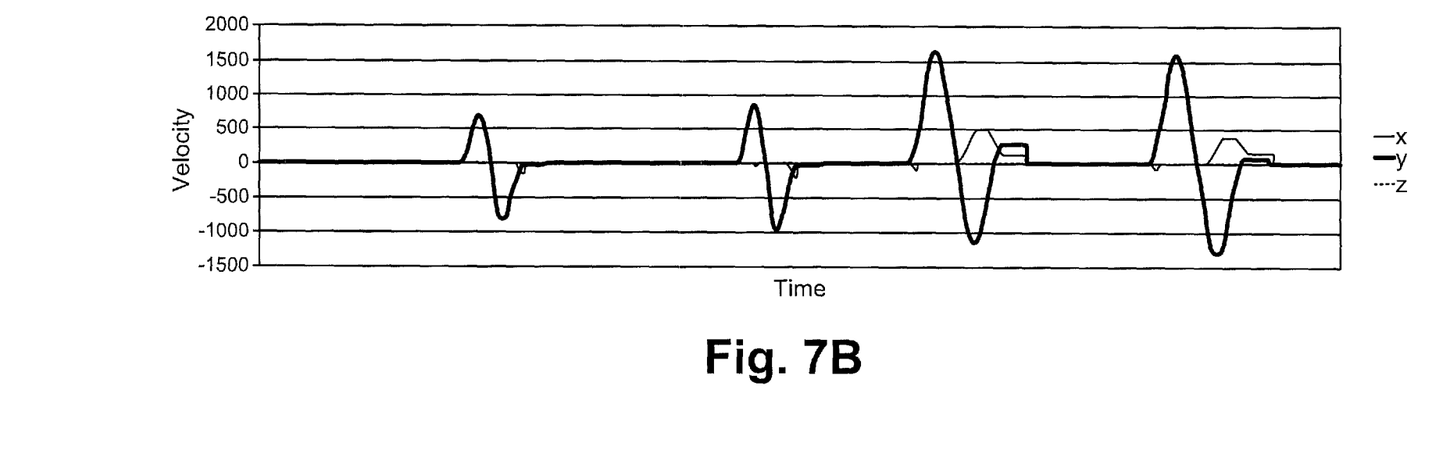
FIG. 7B illustrates a graph showing a calculated velocity value from the acceleration data as depicted in FIG. 7A in accordance with some embodiments.

This process is seen in FIG. 7B which illustrates a velocity value over time for the filtered acceleration data used of a body-worn sensor worn on the arm as depicted in FIG. 7A, such as describe above.

Figure 8A:
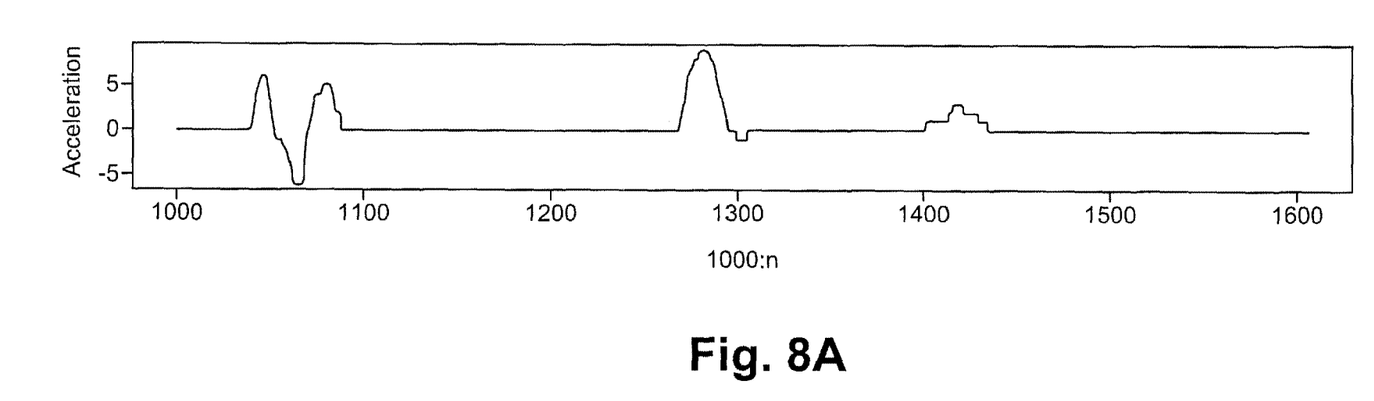
FIG. 8A illustrates a graph showing a signal depicting acceleration over time a body-worn sensor worn on foot in accordance with some embodiments.
Figure 8B:
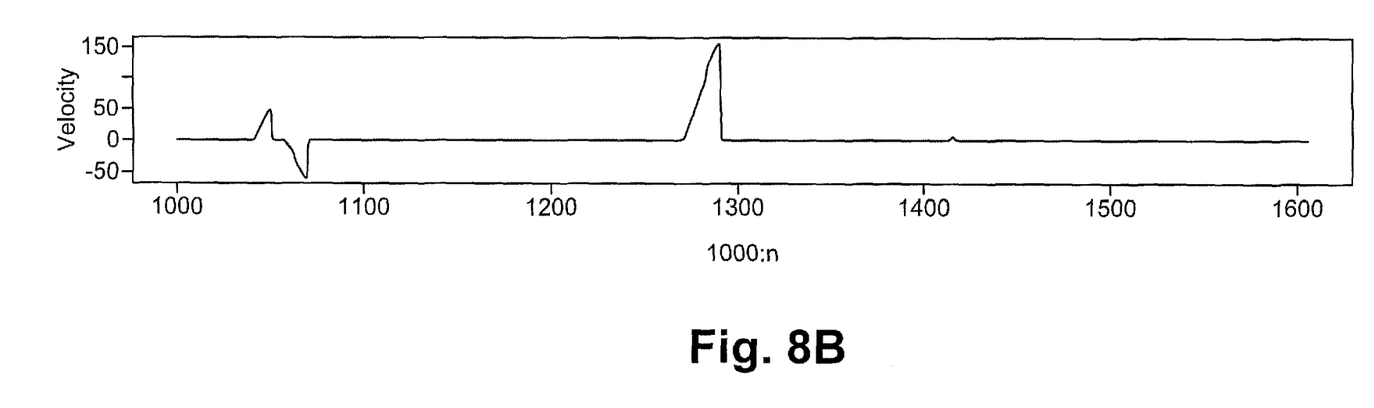
FIG. 8B illustrates a graph showing a calculated velocity value from the acceleration data as depicted in FIG. 8A in accordance with some embodiments.

This process is also seen in FIGS. 8A and 8B which illustrate the acceleration (FIG. 8A) and the calculated velocity (FIG. 8B) value of a kick in three different ways while utilizing a body-worn sensor on the foot. The acceleration values are raw values detected by the accelerometer based upon three movements of the foot. The first movement corresponds to a quick but small kick, generating a large but short-term positive acceleration. This signal will trigger a response in an acceleration based system, however is rejected. The second movement is quick and big kick, which is accepted and the third movement is a slow but big kick. The third movement lasts longer, but the acceleration value is too small and it fails to accumulate enough speed.

Figure 6:
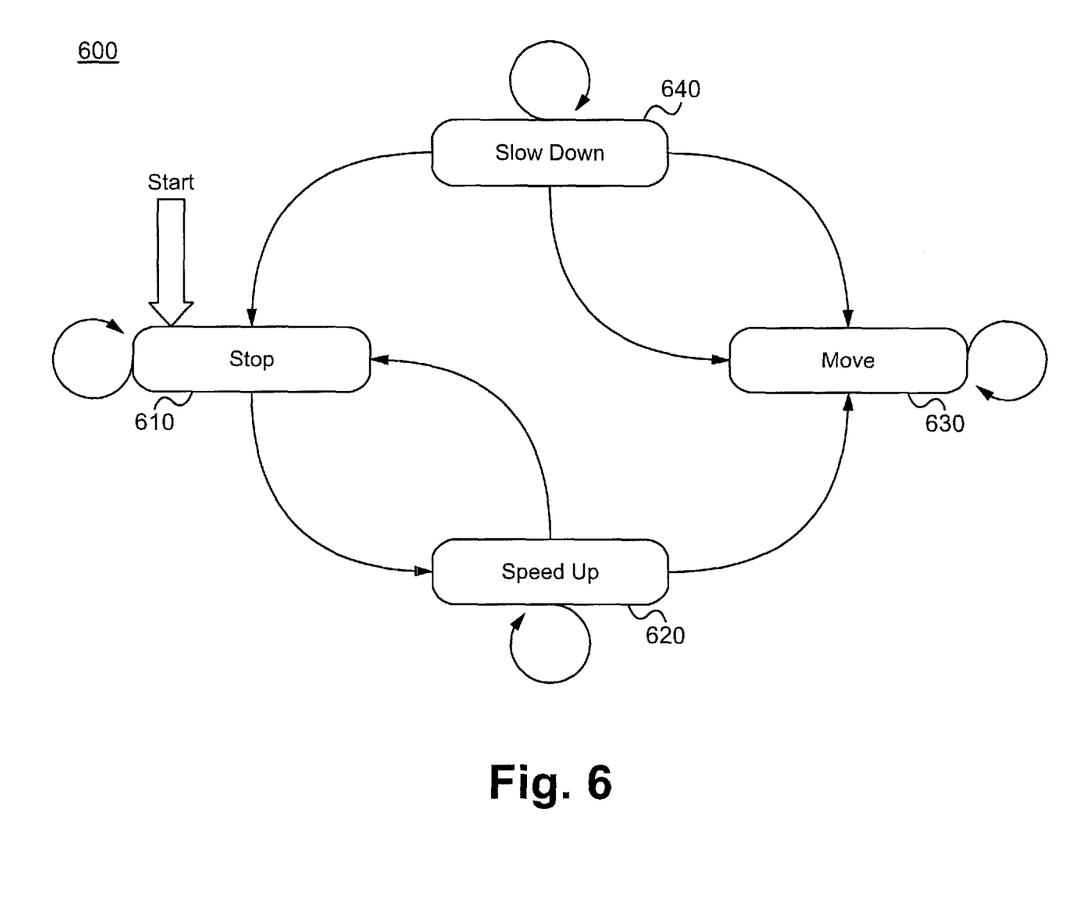
FIG. 6 illustrates a velocity converting state machine in accordance with some embodiments.

After the velocity information or other such processing information is gathered, the system can then move on to classification via a machine learning algorithm. In some embodiments, this comprises a decision tree and state machine such as shown in FIG. 6. In some embodiments, a feature extraction technique is utilized and then applied to a support vector machine. However, other appropriate machine learning algorithms are acceptable as well.

FIG. 6 illustrates the connections of the velocity converting state machine. As shown within FIG. 6, there are four states in the state machine 600; stop 610, speed up 620, move 630, and slow down 640. Transitions between the states correspond to a plausible velocity value. At the stop state 610, depending upon the velocity value, the system either stays at the stop state 610 or transitions to the speed up state 620. At the speed up state 620, there are three possible movements. The system may stay at the speed up state 620, move back to the stop state 610, or transition to the move state 630. The move state 630 is a mirror of the stop state 610. At the move state 630, the system may either stay at the move state 630 or transition to the slow down state 640. The slow down state 640 is a mirror of the speed up state 620. At the slow down state 640, the system may either stay at the slow down state 640, transition back to the move state 630, or transition to the stop state 610. When the system returns to the stop state, the process starts over.

Figure 10:
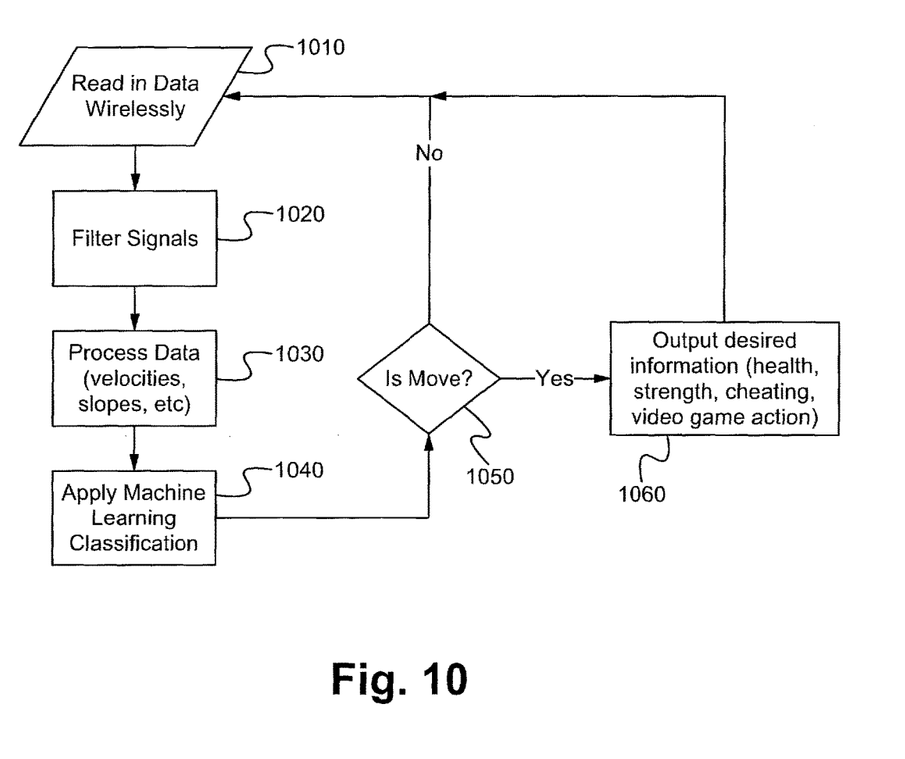
FIG. 10 illustrates a flow chart for detecting and analyzing realistic motion for different end application goals in accordance with some embodiments.

Once the physical movement is determined, the movement can be used to map to whatever output needs to sense the movement. This results in a wide range of end applications such as shown in the flow chart of FIG. 10. FIG. 10 illustrates a method of detecting and analyzing realistic motion for different end application goals.

As shown in FIG. 10, in the step 1010 wireless data is read in. In some embodiments, reading the wireless data comprises detecting an acceleration of a body-worn sensor in one of three orthogonal directions and reading the acceleration data from the body-worn sensor. Then, in the step 1020, the wireless data is filtered and in the step 1030, the data is processed. In the step 1040, a classification is applied to the data. For example, in some embodiments, the classification comprises a machine learning algorithm or an inference processing classification. In the step 1050, based upon the classification, it is determined whether the data indicates a valid three-dimensional physical movement. If the data indicates an invalid move, then the method returns to the beginning at the step 1010, where the wireless data is read in. If the data indicates that the movement is valid then a characteristic of the movement is output at the step 1060. In some embodiments, the output comprises a health or strength information. In some embodiments, the output comprises a video game action, or a cheating determination.

After the information is output, the method returns to the beginning at the step 1010, where the wireless data is read in.

In some embodiments, the information is stored and later animated and the movements simulated. Additionally, in some embodiments, the information is analyzed by scoring it against a template and using the information to simulate further moves or combination of moves and finding the strength and effort expounded along with the health statistics calculated. For example, in some embodiments, a motion is normalized to a set length and compared against a defined template of that length.

Figure 9A:
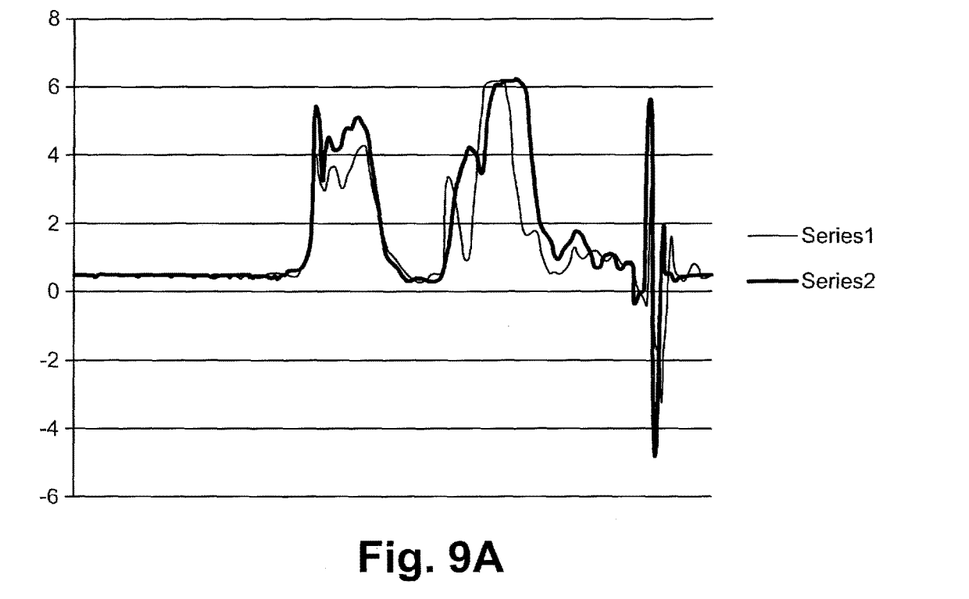
FIG. 9A illustrates a movement of a body-worn sensor plotted against an average movement in accordance with some embodiments.
Figure 9B:
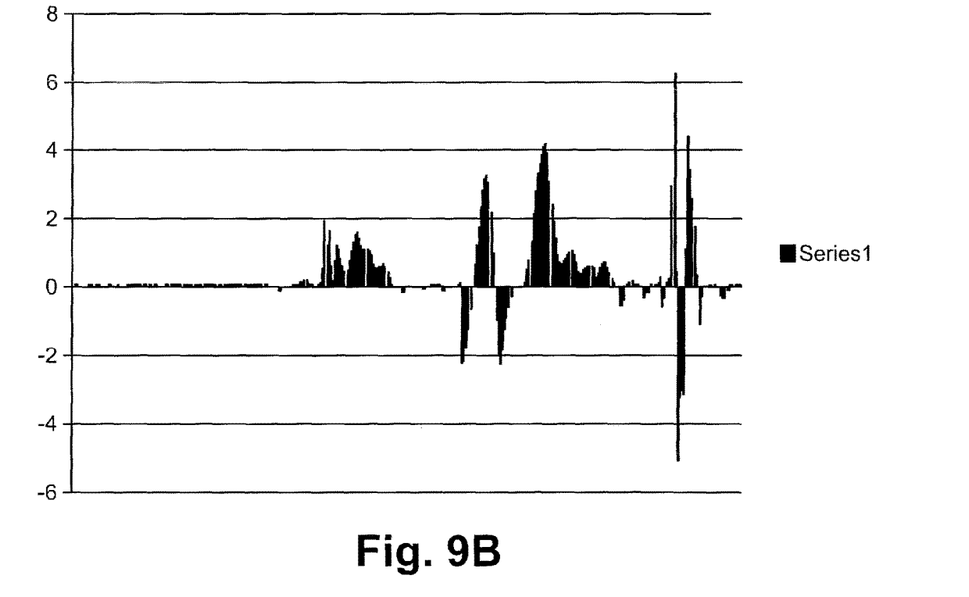
FIG. 9B illustrates the difference between the calculated movement and the average movement as depicted in FIG. 9A in accordance with some embodiments.

As shown in FIGS. 9A and 9B, a movement is plotted against an average and the resulting difference is used to score calculations of the movement. The difference per point is taken and the sum of the absolute value creates a workable heuristic. A point by point difference between a motion curve and a template curve is determined, the absolute value of the difference is taken, and the sum of the difference is used as a score value for the accuracy and effectiveness of the movement. This can then be adapted to a training environment and tool for those who would like to perform realistic sports action. These moves, classified in the motion analysis system listed above, can also be applied to realistic healthy video gaming. In some embodiments, it is used as game input in order to control players in a game.

For example, soccer movements are classifiable into, among others, shooting, running, passing and lobbing movements and the strength of the movements is determined based on the velocity value. Running is separated into two movements depending on the magnitude of the velocity and a small velocity value indicates running while a large magnitude indicates a sprinting motion. If any one of the movements is too small, it is ignored in order to encourage the player to make bigger movements. Additionally, this prevents the user from cheating, which results in healthy exercise.

In some embodiments, hand and leg movements are classified to a basketball game. To move the player in the game, the user needs to keep on running and other foot movements are ignored. Hand movements are detected and classifiable into, among others, passing, shooting, and dribbling. Shooting strength is based on magnitude of the velocity value and a small magnitude can be recognized as a fake shooting.

Figure 11:
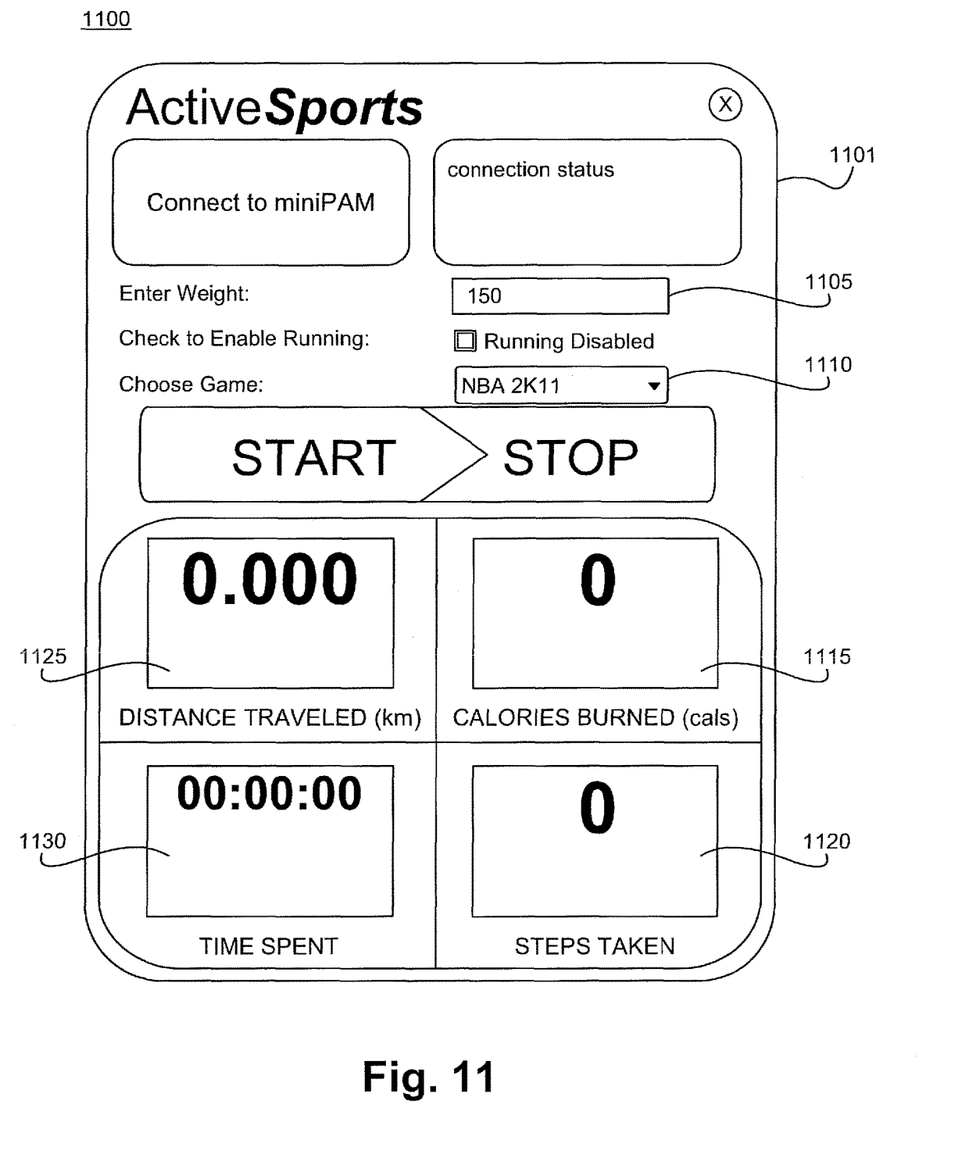
FIG. 11 illustrates a software interface of a system for detecting and classifying body movements in accordance with some embodiments.

With the system, health statistics such as strength and energy expenditure information is outputted to a software interface where it can be displayed to a user. FIG. 11 illustrates a software interface in accordance with some embodiments.

As shown in FIG. 11, the software interface 1100 comprise a weight input box 1105 for a user to input their weight, and a game choice input box 1110 for the user to choose the game to be played. The software interface 1100 also comprises a series of output boxes for displaying strength and expenditure information. For example, as shown in FIG. 11, software interface 1100 displays the amount of calories burned 1115, the number of steps taken 1120, the time spent playing the game 1130 and the distance traveled 1125. Although only four health output displays are shown, the user interface 1100 is able to display any number of appropriate health statistics and game inputs as required and/or desired.

In use, the system and method as described above is used for the detection, analysis, and identification of realistic human body and limb movements during sports actions. For example a body-worn sensor comprising an accelerometer on the foot can be used to play a soccer game or a body-worn sensor comprising an accelerometer on the hand can be used to play a basketball game. The system can then identify limb movements in three different directions: x, y, z in order to execute a pass or shoot a jump shot. Additionally, because the system does not make decisions based on 3-axis acceleration or 3-axis spatial coordination, but rather relies on velocity information, the system is more accurate and harder to cheat against. Consequently, this enables a user to move more and do more exercise when playing the games.

Moreover, the system is able to distinguish between small, large, slow, and fast movements, which is important for sports-related applications and fine grain variability. By breaking down and detecting variable movements the system is able to detect kicking, passing, lobbing, and running by the action itself, as well as the strength of the action. Therefore, a fast running could trigger sprinting, and a strong forward kick could trigger a movement in game with bigger magnitude or greater strength. The detected movements are then mappable as input of a video game, such as, directing players in a soccer or basketball game. Additionally, based upon the movements within the game, the system is then able to display health related information such as calories burned, steps taken, distance, and time played. Consequently, the system comprises multiple uses including collecting the health information, training and monitoring techniques in live usage settings, and as inputs to simulators and video game environments. Accordingly, the system for near-realistic sports motion analysis and activity monitoring as described herein has many advantages.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications can be made in the embodiment chosen for illustration without departing from the spirit and scope of the invention as defined by the claims. Particularly, although the system has been described as applied to a soccer game and a basketball game, the system may be used to detect, analyze and classify movements in any appropriate context and sport.

What is claimed is:

1. A system for detecting and analyzing motion comprising:
    an attachment member for coupling to a portion of a user's body;
    an acceleration module coupled to the attachment member and programmed to detect accelerations of the attachment member along three orthogonal directions and to translate the accelerations into corresponding acceleration values;
    a velocity converter programmed to convert the acceleration values into velocity values along the three orthogonal directions;
    a state machine programmed to determine a state from a plurality of states based on a previous state and the velocity values; and
    a movement detector programmed to translate the velocity values and the state into a three-dimensional movement of the portion of the user's body.

2. The system of claim 1, wherein the movement detector differentiates between a realistic three-dimensional movement and an attempted cheating of the movement.

3. The system of claim 1, further comprising a pressure sensor coupled to the attachment member for providing pressure values to the velocity converter.

4. The system of claim 3, further comprising a reset module for resetting the velocity values when a reset condition is satisfied.

5. The system of claim 4, wherein the reset condition comprises the pressure sensor contacting a surface.

6. The system of claim 4, wherein the reset condition comprises all the acceleration values being within a predetermined range.

7. The system of claim 4, further comprising a gyroscope, wherein the reset module is programmed to adjust for gravity accelerations and gyroscope values to estimate the three dimensional position of the acceleration module.

8. The system of claim 1, further comprising a transmitter for wirelessly transmitting the acceleration values to the velocity converter.

9. The system of claim 1, further comprising a classification module programmed to classify the three-dimensional movement into classified movement.

10. The system of claim 9, wherein the classification module is programmed to classify the three-dimensional movement using a machine learning algorithm or inference processing.

11. The system of claim 9, wherein the classification module is programmed to classify the three-dimensional movement based on a pattern of the velocity values, a direction of the velocity values, or a magnitude of the velocity values.

12. The system of claim 9, wherein the classified movement comprises a sports movement.

13. The system of claim 12, wherein the classified movement comprises a soccer movement, a football movement, a basketball movement, a running movement, a tennis movement, or a baseball movement.

14. The system of claim 1, further comprising a health monitoring module programmed to determine health-related statistics from the three-dimensional movement.

15. The system of claim 1, further comprising an interface programmed to map the three-dimensional movement to movement for an application.

16. The system of claim 15, where the application comprises a video game application, a health-monitor application, an animation application, a simulation application, or a scoring application for scoring the three-dimensional movement against a defined template.

17. A method of detecting and analyzing motion comprising:
    detecting an acceleration of a body-worn sensor coupled to a portion of a user's body in one of three orthogonal directions;
    translating the acceleration into a corresponding acceleration value;
    calculating a velocity value based upon the acceleration of the body-worn sensor;
    determining, by a state machine, a state from a plurality of states based on a previous state and the velocity value; and
    determining a three-dimensional physical movement of the portion of the user's body based upon the calculated velocity value and the state.

18. The method of claim 17, wherein the method further comprises differentiating between a realistic three-dimensional movement and an attempted cheating of the movement.

19. The method of claim 17, further comprising a receiving a pressure value from a pressure sensor.

20. The method of claim 17, wherein the velocity is reset when a reset condition is satisfied.

21. The method of claim 20, wherein the reset condition comprises the pressure sensor contacting a surface.

22. The method of claim 20, wherein the reset condition comprises all the acceleration values being within a predetermined range.

23. The method of claim 20, wherein the reset condition comprises adjusting for gravity accelerations and gyroscope values to estimate a three dimensional position of a sensor.

24. The method of claim 17, further comprising classifying the three-dimensional movement into a classified movement.

25. The method of claim 24, wherein the movement is classified into three-dimensional movement using a machine learning algorithm or inference processing.

26. The method of claim 24, wherein the movement is classified into three-dimensional movement based on a pattern of the velocity values, a direction of the velocity values, or a magnitude of the velocity values.

27. The method of claim 24, wherein the classified movement comprises a sports movement.

28. The method of claim 27, wherein the classified movement comprises a soccer movement, a football movement, a basketball movement, a running movement, a tennis movement, or a baseball movement.

29. A method of detecting and analyzing realistic motion, comprising:
reading wireless data comprising an acceleration detected by a body-worn sensor coupled to a portion of a user's body in at least one of three directions;
filtering the data with some preliminary cheating prevention checks;
processing the data;
applying a classification to the data;
based upon the classification, determining whether the data indicates a valid three-dimensional physical movement including whether the movement is a valid movement or an attempted cheating movement generated from non-realistic motion;
determining, by a state machine, a state from a plurality of states based on a previous state and the wireless data; and
based on a determinations that the movement is valid and the state, outputting a characteristic of the three-dimensional physical movement of the portion of the user's body.

30. The method of claim 29 wherein reading the data comprises:
detecting an acceleration of a body-worn sensor in one of three orthogonal directions; and
reading the acceleration data from the body-worn sensor.

31. The method of claim 29 wherein the classification comprises a machine learning algorithm or an inference processing classification.

32. The system of claim 1, further comprising:
a pressure sensor configured to be attached to a foot of the user's body and configured to correct a non-zero reading of the acceleration module due to a vibration.

33. The system of claim 32, wherein the pressure sensor is configured to reset at least one of the acceleration values to zero in response to a determination that the foot of the user's body is on a ground.

34. The system of claim 1, wherein the movement detector is further programmed to determine whether a magnitude of the three-dimensional movement is lower than a threshold value, and to prevent cheating by ignoring the three-dimensional movement in response to an event of the magnitude of the three-dimensional movement being lower than the threshold value.

35. The system of claim 1, wherein the plurality of states comprise stop, speed up, move, and slow down.

* * * * *